US010632249B2

(12) United States Patent
Marbet et al.

(10) Patent No.: US 10,632,249 B2
(45) Date of Patent: *Apr. 28, 2020

(54) DRUG DELIVERY DEVICE WITH NEEDLE ACTUATION MECHANISM

(71) Applicant: SENSILE MEDICAL AG, Olten (CH)

(72) Inventors: Regina Marbet, Ruetschelen (CH); Daniel Fehlmann, Uerkheim (CH)

(73) Assignee: SENSILE MEDICAL AG, Olten (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/989,392

(22) Filed: May 25, 2018

(65) Prior Publication Data

US 2018/0272059 A1 Sep. 27, 2018

Related U.S. Application Data

(63) Continuation of application No. 14/908,572, filed as application No. PCT/IB2014/063384 on Jul. 24, 2014, now Pat. No. 10,076,605.

(30) Foreign Application Priority Data

Jul. 30, 2013 (EP) .................................... 13178505

(51) Int. Cl.
*A61M 5/142* (2006.01)
*A61M 5/158* (2006.01)
(Continued)

(52) U.S. Cl.
CPC ........ *A61M 5/14248* (2013.01); *A61M 5/158* (2013.01); *A61M 1/1051* (2014.02);
(Continued)

(58) Field of Classification Search
CPC .... A61M 5/14248; A61M 5/158; A61M 5/46; A61M 2005/14252; A61M 2005/1585;
(Continued)

(56) References Cited

U.S. PATENT DOCUMENTS

| 1,958,556 | A | * | 5/1934 | White | D05C 15/00 112/80.04 |
|---|---|---|---|---|---|
| 8,617,108 | B2 | | 12/2013 | Ramadoss et al. | |

(Continued)

FOREIGN PATENT DOCUMENTS

| WO | WO 2008/098246 | 8/2008 |
|---|---|---|
| WO | WO 2009/010399 | 1/2009 |

OTHER PUBLICATIONS

Written Opinion in International Application No. PCT/IB2014/063384, dated Nov. 10, 2014, pp. 1-7.

*Primary Examiner* — Nathan R Price
*Assistant Examiner* — Dung T Ulsh
(74) *Attorney, Agent, or Firm* — Saliwanchik, Lloyd & Eisenschenk

(57) ABSTRACT

A delivery unit (2) of a drug delivery device (1), the delivery unit (2) comprising a subcutaneous delivery mechanism (9) having a subcutaneous delivery member (92), and a subcutaneous delivery member actuation mechanism (10) being operable to move the subcutaneous delivery member (92) between a retracted position and an extended position. The actuation mechanism (10) comprises a rotary member (102) having an engagement member (104) rotatable relative a support member (14), and an actuator (106) comprising a pivot portion (10A) and an engagement portion (10B) pivotally connected to the support member via the pivot portion. The engagement member (104) and engagement portion (10B) are configured to engage upon rotation of the rotary member to pivot the actuator between first and second positions and to thereby move the subcutaneous delivery member (92) between the corresponding retracted and extended positions. In an embodiment, the needle actuation mechanism may comprise a reuse protection.

14 Claims, 9 Drawing Sheets

(51) Int. Cl.
 *A61M 1/10* (2006.01)
 *A61M 5/145* (2006.01)
(52) U.S. Cl.
 CPC ........... *A61M 2005/14252* (2013.01); *A61M 2005/14268* (2013.01); *A61M 2005/14533* (2013.01); *A61M 2005/1585* (2013.01)
(58) Field of Classification Search
 CPC ......... A61M 2005/14268; A61M 2005/14533; A61M 1/1051
 See application file for complete search history.

(56) References Cited

U.S. PATENT DOCUMENTS

| | | |
|---|---|---|
| 2003/0199825 A1 | 10/2003 | Flaherty |
| 2004/0116847 A1 | 6/2004 | Wall |
| 2006/0135908 A1 | 6/2006 | Liniger et al. |
| 2007/0106218 A1 | 5/2007 | Yodfat et al. |
| 2008/0051714 A1 | 2/2008 | Moberg et al. |
| 2008/0051730 A1* | 2/2008 | Bikovsky ............ A61M 5/1413 604/240 |
| 2008/0208139 A1 | 8/2008 | Scheurer et al. |
| 2008/0223592 A1 | 9/2008 | Erhardt et al. |
| 2008/0269687 A1 | 10/2008 | Chong et al. |
| 2008/0319414 A1 | 12/2008 | Yodfat et al. |
| 2010/0217105 A1 | 8/2010 | Yodfat et al. |
| 2010/0228195 A1 | 9/2010 | Kehr et al. |
| 2011/0054390 A1 | 3/2011 | Searle et al. |
| 2011/0166512 A1 | 7/2011 | Both et al. |
| 2011/0238009 A1 | 9/2011 | Meron et al. |
| 2012/0143137 A1 | 6/2012 | Shekalim et al. |
| 2013/0060233 A1 | 3/2013 | O'Connor et al. |
| 2013/0116632 A1 | 5/2013 | Yavorsky et al. |
| 2014/0031793 A1 | 1/2014 | Constantineau et al. |
| 2014/0257241 A1 | 9/2014 | Sutkin et al. |
| 2014/0296825 A1 | 10/2014 | Lemaire et al. |
| 2015/0047474 A1 | 2/2015 | Abel |
| 2015/0080798 A1 | 3/2015 | Nzike et al. |
| 2015/0126926 A1 | 5/2015 | Giambattista et al. |
| 2015/0306307 A1 | 10/2015 | Cole et al. |
| 2016/0213838 A1 | 7/2016 | Schabbach et al. |
| 2016/0213839 A1 | 7/2016 | Schabbach et al. |
| 2016/0213840 A1 | 7/2016 | Schabbach et al. |

* cited by examiner

Figure 10
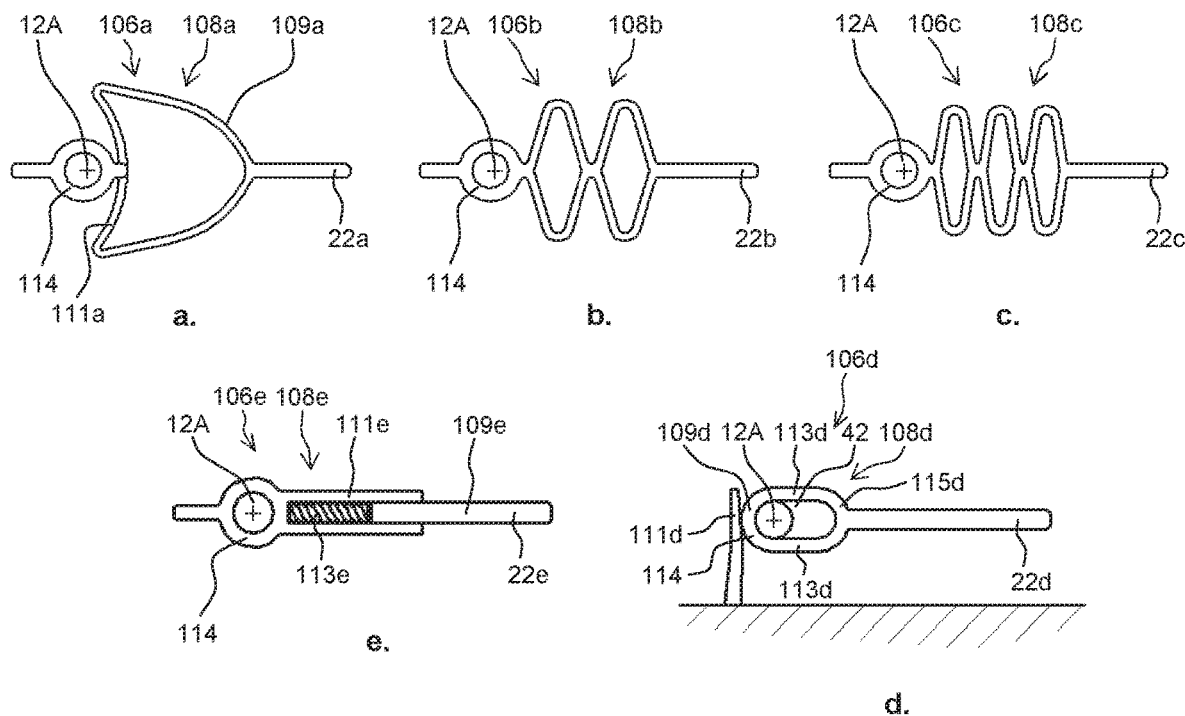
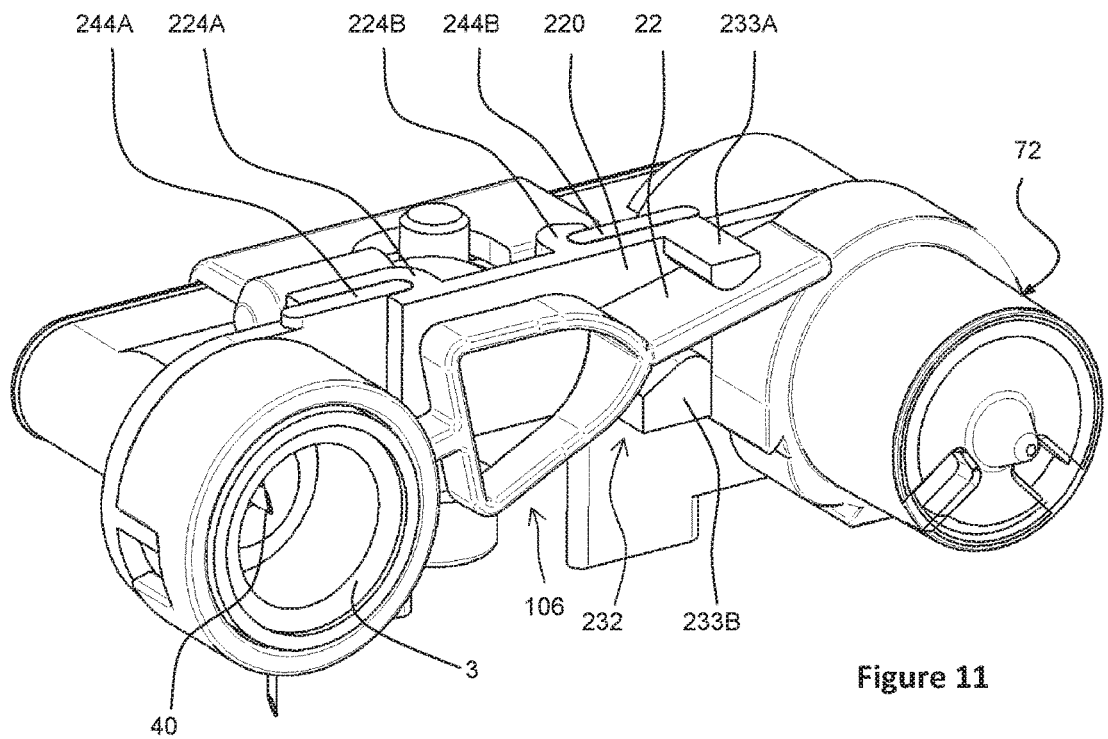
Figure 11

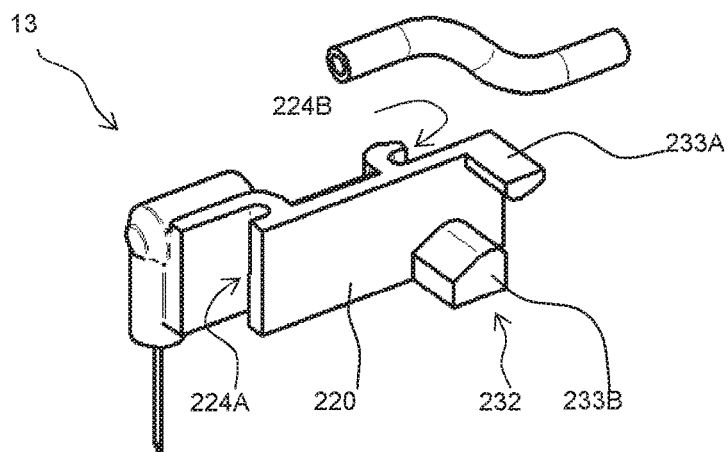
Figure 12
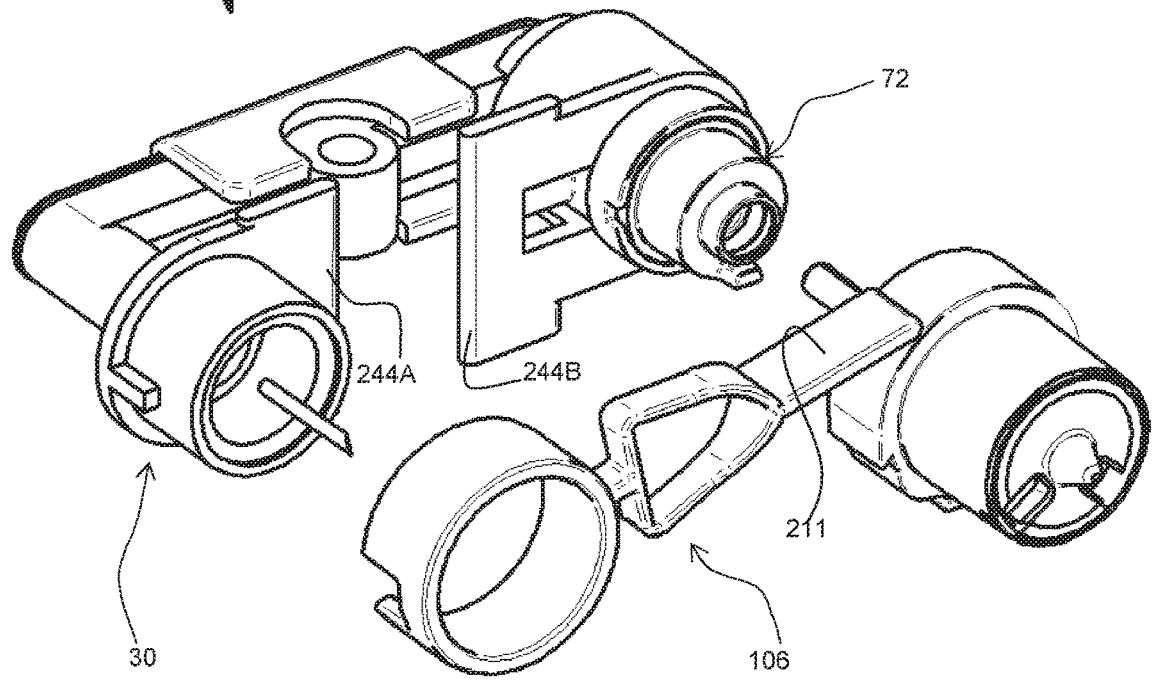
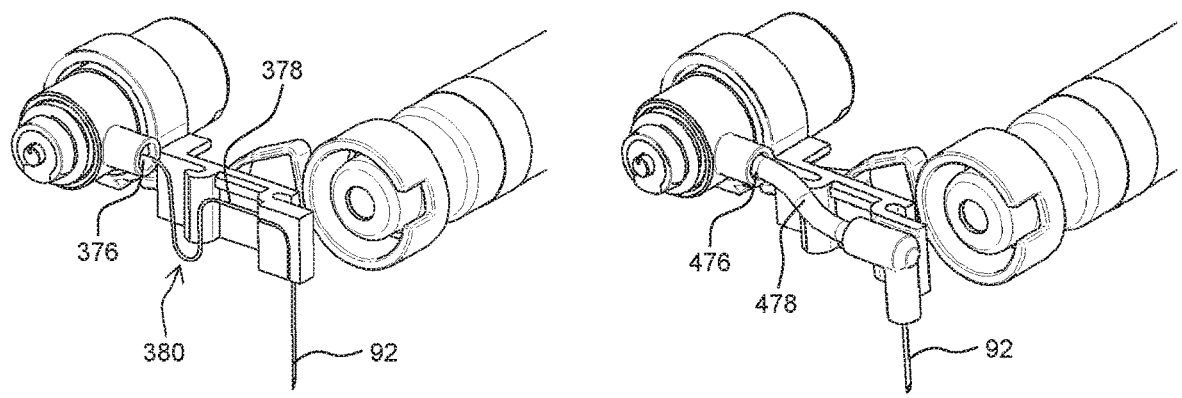
Figure 13
Figure 14

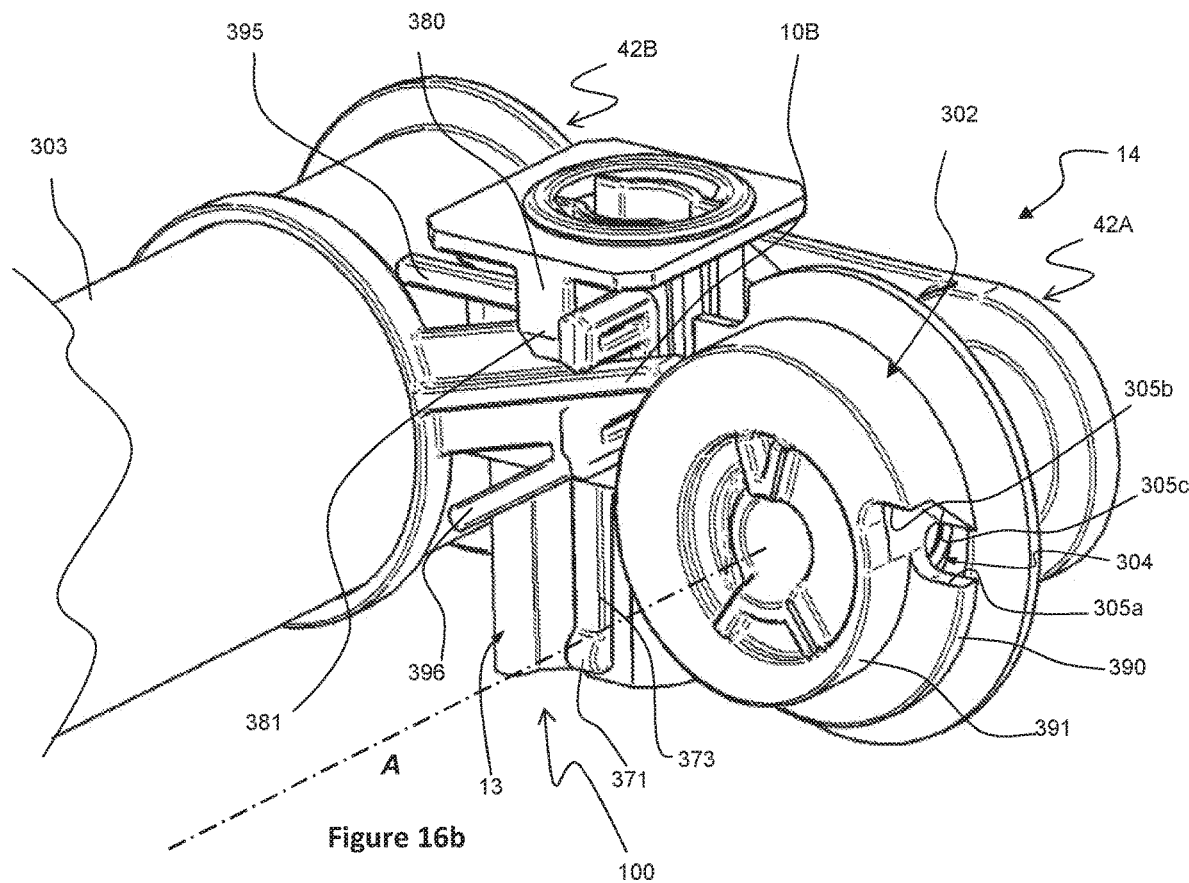
Figure 16b
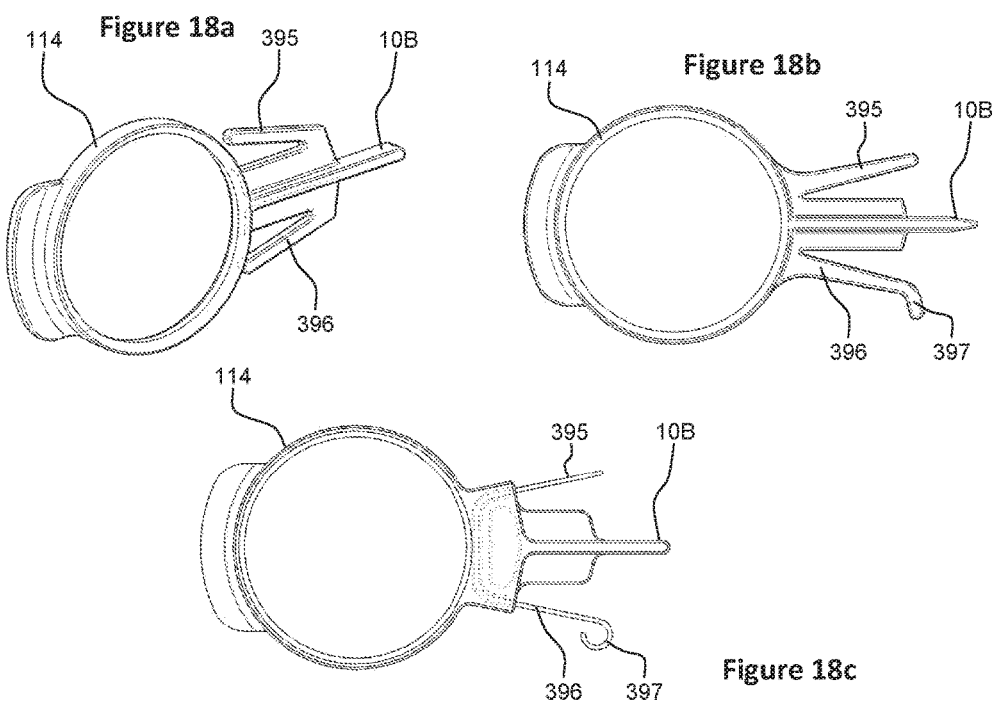
Figure 18a
Figure 18b
Figure 18c

Park position

Needle insertion

Needle insertion - complete

Drug delivery

Needle retraction

End position

Figure 19   Park position

DRUG DELIVERY DEVICE WITH NEEDLE ACTUATION MECHANISM

CROSS-REFERENCE TO RELATED APPLICATIONS

This application is the continuation of U.S. application Ser. No. 14/908,572, filed Jan. 29, 2016, which is the U.S. national stage application of International Patent Application No. PCT/IB2014/063384, filed Jul. 24, 2014.

TECHNICAL FIELD

The present invention relates to a drug delivery device for subcutaneously delivering a medicament, and in particular to a drug delivery device with a needle actuation mechanism.

DESCRIPTION OF RELATED ART

The regular trans-dermal administration of doses of a medicament is necessary for the control or therapy of many conditions, such as diabetes, growth hormone deficiency, pain therapy, and chemotherapy. For instance, diabetic patients may require injections of insulin several times a-day. The insulin dosage regimen required for a diabetic patient varies depending on a number of factors including, for instance, the type of diabetes, the type of insulin administered, the actual severity of the condition, the lifestyle of the patient, the routine and diet of the patient. Accordingly diabetic patients often need to administer doses of insulin themselves, several times a day, and in places other than hospitals or medical centres.

A number of drug delivery devices have been developed to facilitate the self-administration of medicaments. Such devices may comprise needle actuation mechanisms which can be operated to cause a needle to be automatically inserted into a user.

One such example is given in US 2011/0166512 which discloses a drug delivery device with an actuation mechanism that comprises a motor which is arranged to drive, via a gear set, a push rod. In more detail, the rotary action of the motor is geared down by the gear set and converted to linear motion by means of a rack and pinion. The rack extends along a portion of the push rod, such that the push rod provides linear motion to extend and retract a needle connected thereto.

Another mechanism is disclosed in US 2004/0116847, wherein the actuation mechanism has a drive means in the form of a spring, electric or pneumatic system. In more detail, before use, a needle is held in a retracted position and during use the drive means causes the needle be driven to an extended delivery position. During the driving movement, the reservoir is driven to move with the needle such that when arrested an inertial force of the reservoir is sufficient to cause it to be perforated by an end of the needle. The drive means thereafter applies a force to the perforated reservoir to cause the medicament to be dispensed through the opposite end of the needle. The device may also include a spring operated system for retracting the needle.

Yet another mechanism is disclosed in US 2013/0060233, wherein a pre-compressed insertion spring is arranged to insert the needle, and a pre-compressed retraction spring is used to retract the needle.

These drug delivery devices however have a number of drawbacks.

The motor driven actuation mechanism of US 2011/0166512 requires a complex and bulky arrangement of gears and a rack and pinion arrangement. Moreover, to achieve a fast extension and retraction action, which desirably limits discomfort felt by a patient, a large amount of power would be required by the motor.

The actuation mechanisms of US 2004/0116847 and US 2013/0060233 require pre-charging before use, for instance, by compression of a spring. This generally limits their use to the application of a single dosage.

Depending on the application, a drug may need to be administered in multiple doses during the course of a day, or in a continuous mode, or a combination of both basal and bolus administration. Moreover depending on the application, a drug may need to be administered over an extended period of time and in this regard it would be desirable not to have to replace the drug delivery device more often than would be reasonably needed for hygiene, safety or physiological tolerance reasons.

Important factors for drug delivery devices include:
the safety, ease and low pain of connecting the device to the patient,
the safety, ease and low pain of disconnecting the device from the patient, and
the comfort of the device worn by the patient, especially when the device should be worn for a few days or longer before replacement.

An object of the invention is to provide a drug delivery device that is portable, easy and safe to use, and does not require complex manipulations by the user.

It would be advantageous to provide a drug delivery device that is comfortable to connect, to wear, and to disconnect.

It would be advantageous to provide a drug delivery device with a protection against reuse of a subcutaneous delivery member.

It would be advantageous to provide a drug delivery device that is reliable and compact.

It would be advantageous to provide a drug delivery device that is cost-effective to manufacture, such that it may be manufactured, at least in part, as a non-reusable disposable device.

SUMMARY OF THE INVENTION

Disclosed herein and according to a first aspect of the invention is a delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position. In the extended position the subcutaneous delivery member is arranged to deliver a dosage of a fluid trans-dermally to a patient and in the retracted position the subcutaneous delivery member is arranged such that it is retracted from the patient. The actuation mechanism comprises a rotary member rotatable relative to a support member, the rotary member having an engagement member, and an actuator pivotally connected to the support member, the actuator having an engagement portion. The engagement member and engagement portion are configured to engage upon rotation of the rotary member and the actuator is configured such that the engagement causes a subcutaneous delivery member actuation portion of the actuator to pivot between first and second positions, and to thereby move the subcutaneous delivery member between the corresponding retracted and extended positions.

Advantageously, since the actuation mechanism is actuated by rotation of the rotary member it can be driven by an angular displacement of a pump engine which may be used to pump a dosage of a drug to the subcutaneous delivery member. Moreover, the actuation mechanism comprises relatively few components and is therefore compact and can be manufactured cost effectively. A further advantage is that the subcutaneous delivery member can be moved very quickly between first and second positions, thus reducing pain perceived by the patient.

Preferably, the engagement member of the rotary member and engagement portion of the actuator are configured such that rotation of the rotary member in a first direction causes the actuation portion of the actuator to move the subcutaneous delivery member from the retracted position to the extended position, and preferably such that rotation of the rotary member in a second direction causes the actuation portion of the actuator to move the subcutaneous delivery member from the extended position to the retracted position.

Advantageously, the actuation mechanism is conveniently operated to retract and extend by reversing the direction of rotation of the rotary member.

Preferably, the actuation mechanism further comprises a subcutaneous delivery member support unit supporting the subcutaneous delivery member, the actuation portion of the actuator being configured to engage with an actuator engagement member of the support unit such that the pivoting of the actuation portion between a first and second position causes the support unit to move the subcutaneous delivery member between the corresponding retracted and extended positions, wherein the support unit is adapted for linear motion by means of a first guide member which is slideably engaged with a second guide member of the support member.

Advantageously, the support unit is operable to convert the pivoting movement of the actuator to a linear movement. A linear movement is beneficial for trans-dermal penetration with the subcutaneous delivery member.

Preferably, the delivery unit further comprises a pump engine configured to pump a fluid from a reservoir to the subcutaneous delivery member by means of a rotary action, wherein the rotation of the pump is connected to the rotation of the rotary member.

In this way the rotary action of the pump or rotary member can be used to actuate the other of the pump or rotary member. Advantageously, driving the pump, for example, also drives the actuation mechanism. The rotatable connection may be achieved by connecting the rotary member to a drive shaft of the pump or by an intermediate gear assembly.

In an embodiment, the engagement portion of the actuator comprises an extension, and the engagement member of the rotary member is disposed around part of a circumference of the rotary member, the engagement member comprising a first portion, the actuator and first portion being configured such that the first portion receives the extension when the rotary member is rotated in a first direction and the extension is arranged on a first side of a line between an axis of rotation of the rotary member and the pivot, and being further configured such that upon further rotation in the first direction the extension is moved from the first extension position to a second extension position. In the second extension position the extension is arranged on an opposed second side of a line between the axis of rotation of the rotary member and the pivot, the actuator being configured such that the first extension position corresponds to the actuation portion in the first position and the second extension position corresponds to the actuation portion in the second position.

Preferably, the engagement member and extension of the actuator are configured such that when the extension is in the second extension position, rotation in the first direction does not substantially move the actuation portion of the actuator.

Advantageously, once the actuation portion is moved to the second position, the rotary member may continue to rotate in the first direction without affecting the position of the subcutaneous delivery member. In this way precise control of the rotational position of the rotary member is not required. Moreover, in the event that the pump engine is used to rotate the rotary member, the pump may continue to operate, with the rotary member driven in the first direction, to deliver the required dosage. It may also be stopped and restarted in the same direction of rotation over a given time to deliver a specific dosage regimen whilst the subcutaneous delivery member remains extended.

In an embodiment, the engagement member of the rotary member may further comprise a second portion, the actuator and second portion being configured such that the second portion receives the extension when the rotary member is rotated in a second direction and the extension is arranged on the second side of a line between an axis of rotation of the rotary member and the pivot, and being further configured such that upon further rotation in the second direction the extension is moved from the second extension position to the first extension position.

Advantageously, once the actuator is returned to the first position, the rotary member may continue to rotate in the second direction without affecting the position of the subcutaneous delivery member. In this way precise control of the rotational position of the rotary member is not required.

In an embodiment, the first portion may comprise an angled catch or other obstacle or interference which for instance protrudes outwardly in a radial direction to catch the engagement portion of the actuator. Similarly, the second portion may comprise an angled catch, shoulder, or other obstacle or interference which for instance protrudes outwardly in a radial direction. A lip may be circumferentially disposed between the first and second portions.

Preferably, the subcutaneous delivery member actuation mechanism comprises a deformable member, the deformable member being configured to deform on engagement of the engagement portion of the actuator with the engagement member of the rotary member, to enable relative displacement between the engagement portion and engagement member to enable the actuation portion of the actuator to move between the first and second positions. The deformable portion may be elastically displaceable to allow the actuation portion to snap between the first and second positions in a bi-stable manner. Snapping between the first and second positions causes the subcutaneous delivery member to be rapidly inserted and retracted such that minimum discomfort is experienced by the patient. However, it will be appreciated that it is within the scope of the invention that the deformable portion enables the actuation portion of the actuator to elastically move between the first and second positions without a snapping action.

In one embodiment, the deformable member comprises a deformable portion arranged on the rotary member, the deformable portion being configured such that on engagement the engagement member of the rotary member displaces relative to the engagement portion of the actuator.

In another embodiment, the deformable member comprises a deformable portion arranged on the actuator, the deformable portion being configured such that on engagement the engagement portion of the actuator displaces relative to the engagement member of the rotary member. For instance, the deformable portion is elastically displaceable to allow the actuation portion to snap between the first and second positions in a bi-stable manner.

In an embodiment, the actuator may comprise at a second portion the engagement portion, at a first portion the pivoted connection, and an elongated axis extending there between, the deformable portion being configured to deform axially along the elongated axis. Advantageously, deformation of the deformable portion along the elongated axis enables the actuator to contract when the extension moves with the rotary member between the first and second extension positions.

In an embodiment, the deformable portion comprises an elastic bow portion defining an interior region, the elastic bow portion being arranged such that it may at least partially collapse into the interior region. The elastic bow portion may, for instance, comprise one or more diamond shapes such as a rhombic shape or one or more shapes having a first curved portion that extends around a second curved or straight portion. The deformable portion is preferably biased into an un-deformed extended position by means of the material elasticity and optionally the geometry.

In an embodiment, the deformable portion comprises a first guide member at a first end of the deformable portion which is adapted to slideably engage with a second guide member at a second end of the deformable portion. The first guide member and second guide member may, for instance, correspond to a piston adapted to slide within a housing. Alternatively, the first guide member and second guide member may correspond to an insert slideable within a channel. A biasing means preferably biases the first and second guide member into an un-deformed extended position. The biasing member may, for example, comprise a spring or pneumatic system.

Preferably, the actuator comprises a stop engageable with a portion of a support member to prevent over-extension and/or retraction of the actuation portion and therefore the subcutaneous delivery member.

The delivery unit further may comprise a coupling system having a coupling extension that comprises an exterior defining a bearing surface for pivotally supporting an annular ring of the pivot portion of the actuator to define the pivoted connection, and an interior reservoir head mounting portion for coupling a reservoir to the delivery unit.

Advantageously, the coupling system may comprise a reservoir coupling extension which forms part of the pivoted connection for the actuator and is operable to couple the reservoir to the delivery unit.

In an embodiment, the delivery unit is configured as a disposable unit removeably connectable to a reusable base unit.

According to another aspect of the invention there is provided a drug delivery device comprising the delivery unit according to the first aspect of the invention and a base unit. The base unit may comprise a pump drive configured to drive a pump engine of the reusable base unit. The base unit may comprise a support member arranged to support a reservoir for fluid to be dispensed from the delivery unit. The support member may be arranged to support the reservoir such that as the disposable unit and delivery unit are connected, a head portion of the reservoir is received by a reservoir head mounting portion of a coupling system of the disposable unit. In this way connection of the disposable unit and base unit connects the reservoir to the disposable unit. Alternatively, the disposable unit is arranged such that a head portion of a coupling system receives the reservoir prior to connecting the base unit and disposable unit.

Advantageously, the delivery unit comprises components which are cost-effective to manufacture such that it may be economically disposed of after the required dosage regimen has been delivered. However, the base unit can be retained and attached to a further delivery unit for the delivery of subsequent dosage regimens.

According to a further aspect of the invention there is provided a delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position, wherein in the extended position the subcutaneous delivery member is arranged to deliver a dosage of a fluid trans-dermally to a patient and in the retracted position the subcutaneous delivery member is arranged such that it is retracted from the patient. The actuation mechanism comprises a rotary member rotatable relative to a support member, the rotary member having an engagement member, an actuator connected to the support member, the actuator having an engagement portion, and a pump engine configured to deliver a fluid to the subcutaneous delivery member, the pump being rotatably drivable. The engagement member and engagement portion are configured to engage upon rotation of the rotary member and the actuator is configured such that the engagement causes a subcutaneous delivery member actuation portion of the actuator to move between first and second positions, and to thereby move the subcutaneous delivery member between the corresponding retracted and extended positions, and wherein the rotation of the pump engine is connected to the rotation of the rotary member.

Advantageously, the rotational drive of the pump can simultaneously drive the actuation mechanism. The actuation mechanism of this aspect of the invention may comprise an actuator which is pivotally connected to a support member as described herein. Alternatively, another suitable actuation mechanism may be used. For example, the rotary member may comprise or be connected to a pinion that engages with a rack connected to the subcutaneous delivery member such that rotary action of the rotary member can be used to actuate the subcutaneous delivery member linearly between the extended and retracted position.

According to a further aspect of the invention there is provided a method of administering a medicament to a patient using a delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position, wherein in the extended position the subcutaneous delivery member is arranged to deliver a dosage of a fluid trans-dermally to a patient and in the retracted position the subcutaneous delivery member is arranged such that it is retracted from the patient, the actuation mechanism comprising a rotary member rotatable relative to a support member, the rotary member having an engagement member, an actuator pivotally connected to the support member, the actuator having an engagement portion, and a pump engine configured to deliver a fluid to the subcutaneous delivery member. The engagement member and engagement portion are configured to engage upon rotation of the rotary member and the actuator is configured such that the engagement causes a subcutaneous delivery member actuation portion of the actuator to pivot between first and second positions, and to thereby move the subcutaneous delivery member between the corresponding retracted and extended positions. The method comprises rotating the rotary member in a first direction to cause the actuation portion of the actuator to pivot from the first position to the second position, and to thereby move the subcutaneous delivery member from the retracted position to the extended position.

The method may further comprise actuating the pump engine to supply a fluid to the subcutaneous delivery member.

In an embodiment, the method may further comprise a step of rotating the rotary member in a second direction to cause the actuation portion of the actuator to pivot from the second position to the first position, and to thereby move the subcutaneous delivery member from the extended position to the retracted position.

According to a further aspect of the invention there is provided a method of administering a medicament to a patient using a delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position, wherein in the extended position the subcutaneous delivery member is arranged to deliver a dosage of a fluid trans-dermally to a patient and in the retracted position the subcutaneous delivery member is arranged such that it is retracted from the patient, the actuation mechanism comprising a rotary member rotatable relative to a support member, the rotary member having an engagement member, an actuator connected to the support member, the actuator having an engagement portion, and a pump engine configured to deliver a fluid to the subcutaneous delivery member, the pump being rotatably drivable. The engagement member and engagement portion are configured to engage upon rotation of the rotary member and the actuator is configured such that the engagement causes a subcutaneous delivery member actuation portion of the actuator to move between first and second positions, and to thereby move the subcutaneous delivery member between the corresponding retracted and extended positions, and wherein the rotation of the pump engine is connected to the rotation of the rotary member. The method comprises actuating the pump engine and rotary member to rotate in a first direction to cause the actuation portion of the actuator to move from the first position to the second position, and to thereby move the subcutaneous delivery member from the retracted position to the extended position.

The method may further comprise rotating the pump engine to supply a fluid to the subcutaneous delivery member.

In an embodiment, the method may further comprise a step of rotating the pump engine and rotary member in a second direction to cause the actuation portion of the actuator to move from the second position to the first position, and to thereby move the subcutaneous delivery member from the extended position to the retracted position.

With the subcutaneous delivery member in the retracted position, rotation of the pump engine in the second direction may cause fluid to be pumped through the pump engine in the opposite direction to that of a dispensing direction.

In an embodiment, the delivery unit may be configured such that the pump engine when rotated in a second direction is operable to cause fluid to be transferred from a supply tank to a reservoir, wherein the reservoir is arrangeable in fluid communication with an inlet of the pump engine of the delivery unit, and wherein the outlet of the pump engine is arrangeable in fluid communication with the supply tank. In this way operation of the pump in the second direction can fill the reservoir from the supply tank with fluid to be dispensed by the subcutaneous delivery member.

A supply tank conduit to interconnect the supply tank and pump outlet may comprise a two way valve configured to allow fluid in the supply tank conduit to travel in a direction from the supply tank to the pump engine outlet. In this way operation of the pump engine in the second direction causes fluid from the supply tank to be transmitted, through the supply tank conduit, to the pump engine outlet and to the reservoir. The fluid from the supply tank is not, for instance, pumped to a delivery conduit that interconnects the subcutaneous delivery member and pump outlet. A delivery conduit interconnecting the subcutaneous delivery member and pump outlet may comprise a one way valve configured to allow fluid in the delivery conduit to travel in a direction from the pump engine outlet to the subcutaneous delivery member. In this way operation of the pump engine in the first direction causes fluid from the reservoir to be transmitted, via the pump engine outlet, through the delivery conduit and to the subcutaneous delivery member. The fluid from the reservoir is not, for instance, pumped to the supply tank conduit. The supply tank conduit may be removably connectable to the supply tank.

According to an exemplary embodiment, the rotary member may comprise a first track and a second track around an outer circumference of the rotary member; the first track being configured to guide the actuator in the first direction of rotation of the rotary member and the second track being configured to guide the actuator in a second opposite direction of rotation of the rotary member, and wherein the engagement portion comprises a cam portion operable to axially displace the actuator, when the rotary member turns in the second rotation direction, from the first track to the second track.

The actuation mechanism further comprises a locking protrusion secured to the support and configured to restrict the actuator from moving back from the second track to the first track when in a retracted position after first use.

The needle support member and support body may advantageously comprise a releasable connection formed by a protrusion engaging in a recess configured for releasably holding the needle support member in the extended position. At least one of the protrusion or recess is preferably elastically deformable or elastically supported.

In an embodiment, the actuator may advantageously comprise spring arms configured to elastically bias against a portion of the support in the extended and retracted positions of the needle support member.

Various features herein may be combined with one or more of the above aspects to provide combinations other than those specifically illustrated and described. Further objects and advantageous features of the invention will be apparent from the claims, from the detailed description, and annexed drawings.

BRIEF DESCRIPTION OF THE DRAWINGS

For a better understanding of the invention, and to show how embodiments of the same may be carried into effect, reference will now be made, by way of example, to the accompanying diagrammatic drawings in which:

FIG. 10 is a side view of various actuator configurations that comprise part of the subcutaneous delivery mechanism of FIG. 3.

FIG. 11 is a view in perspective of an alternative embodiment of the subcutaneous delivery mechanism.

FIG. 12 is an exploded view in perspective of the delivery unit of FIG. 11.

FIGS. 13 and 14 are views in perspective of alternative embodiments of the subcutaneous delivery mechanism.

FIG. 16b is another perspective view of a portion of the delivery unit of FIG. 16a.

FIG. 18a is a perspective view of an embodiment of an actuator according to the present invention.

FIG. 18b is a perspective view of another embodiment of an actuator according to the present invention.

FIG. 18c is a perspective view of yet another embodiment of an actuator according to the present invention.

FIG. 19 is an alternative embodiment of a rotary member illustrated in a storage position of the drug delivery device.

DETAILED DESCRIPTION OF EXEMPLARY EMBODIMENTS

Figure 1:
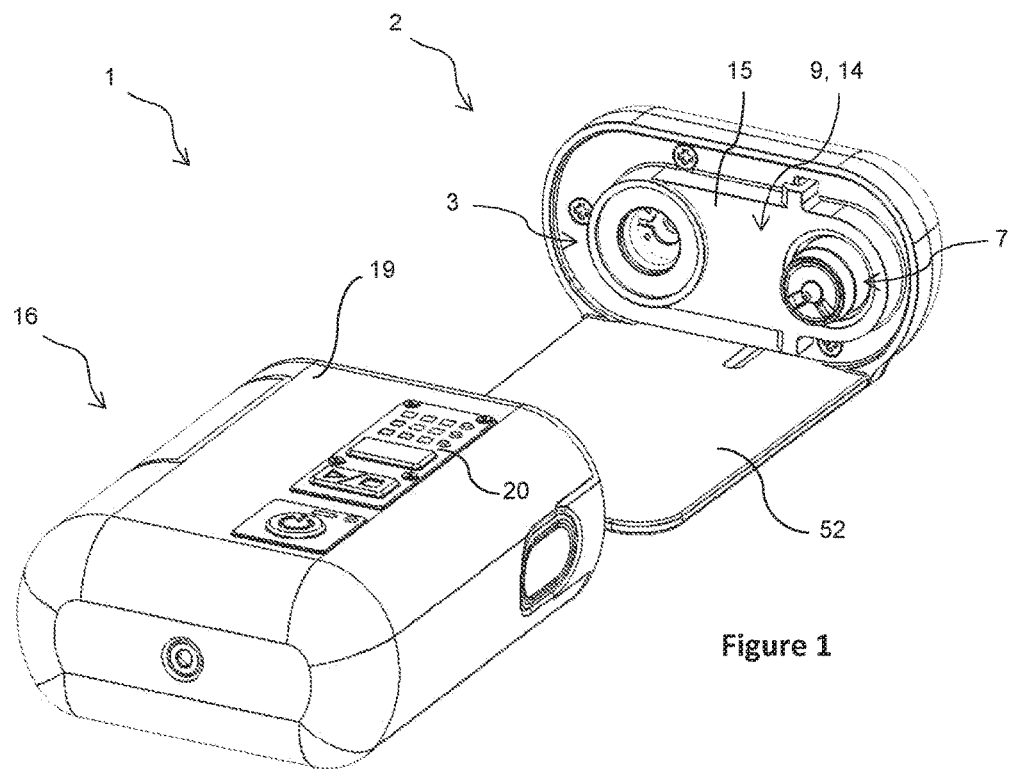
FIG. 1 is a view in perspective of a drug delivery device comprising a base and a delivery unit according to an embodiment of the invention.

Referring to the figures, and in particular to FIGS. 1-2, 16a and 16b, a drug delivery device 1 comprises a delivery unit 2 and a base unit 16. In this embodiment the delivery unit 2 is a disposable unit 2 and is removably connected to the base unit 16 which may be re-usable, although it will be appreciated that in other embodiments they may be formed integrally. The delivery unit 2 comprises a subcutaneous delivery mechanism 9 to deliver a fluid trans-dermally, a reservoir coupling system 3 to couple with a reservoir 303 for containing the fluid within the delivery unit 2, a pump 7 to transfer the fluid from the reservoir to the subcutaneous delivery mechanism 9, and a support member 14 for supporting the aforementioned components. The base unit 16 comprises a pump drive (not shown), a control unit 20 and a housing 19. The housing 19 accommodates the reservoir when received by the coupling system 3. The base unit 16 may also comprise a support member (not shown) to support the reservoir.

Figure 2:
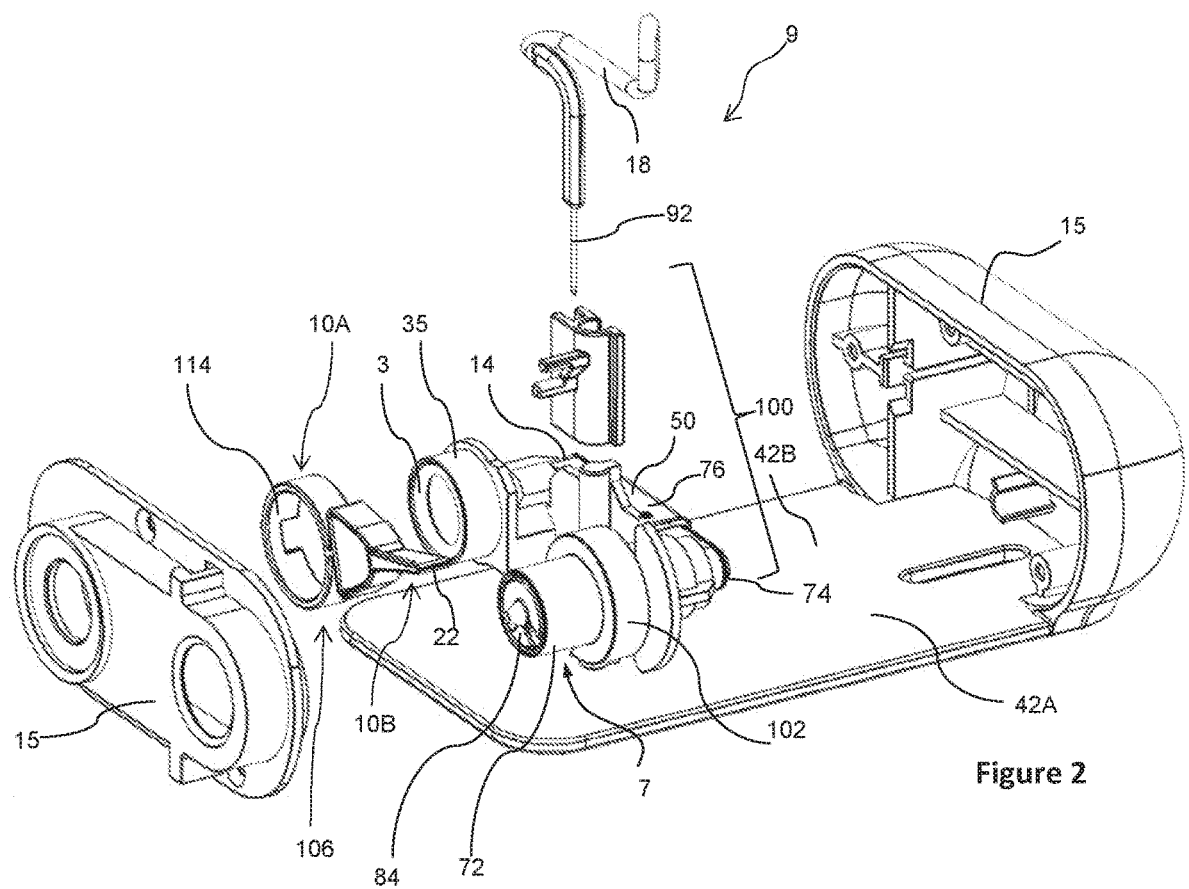
FIG. 2 is an exploded view in perspective of the delivery unit of FIG. 1.
Figure 3:
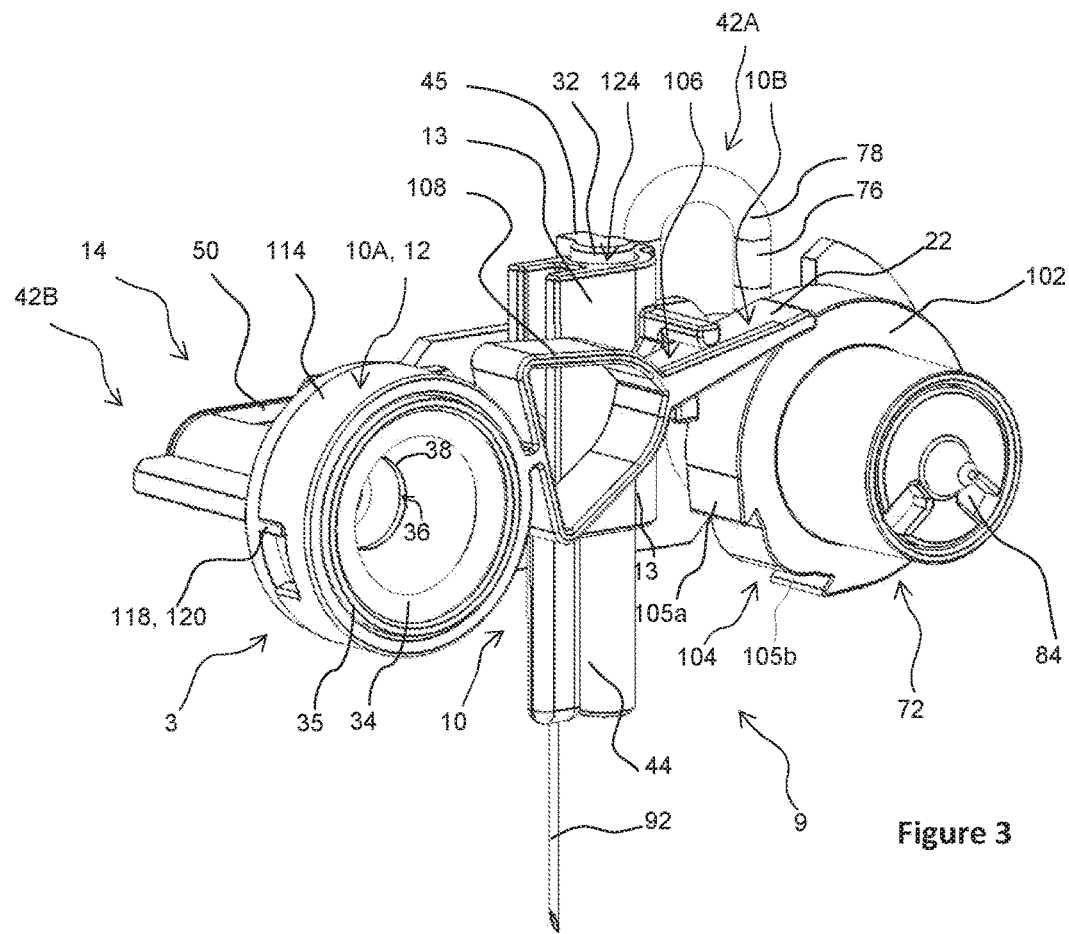
FIG. 3 is a view in perspective of a subcutaneous delivery mechanism of the drug delivery unit of FIG. 2.
Figure 4:
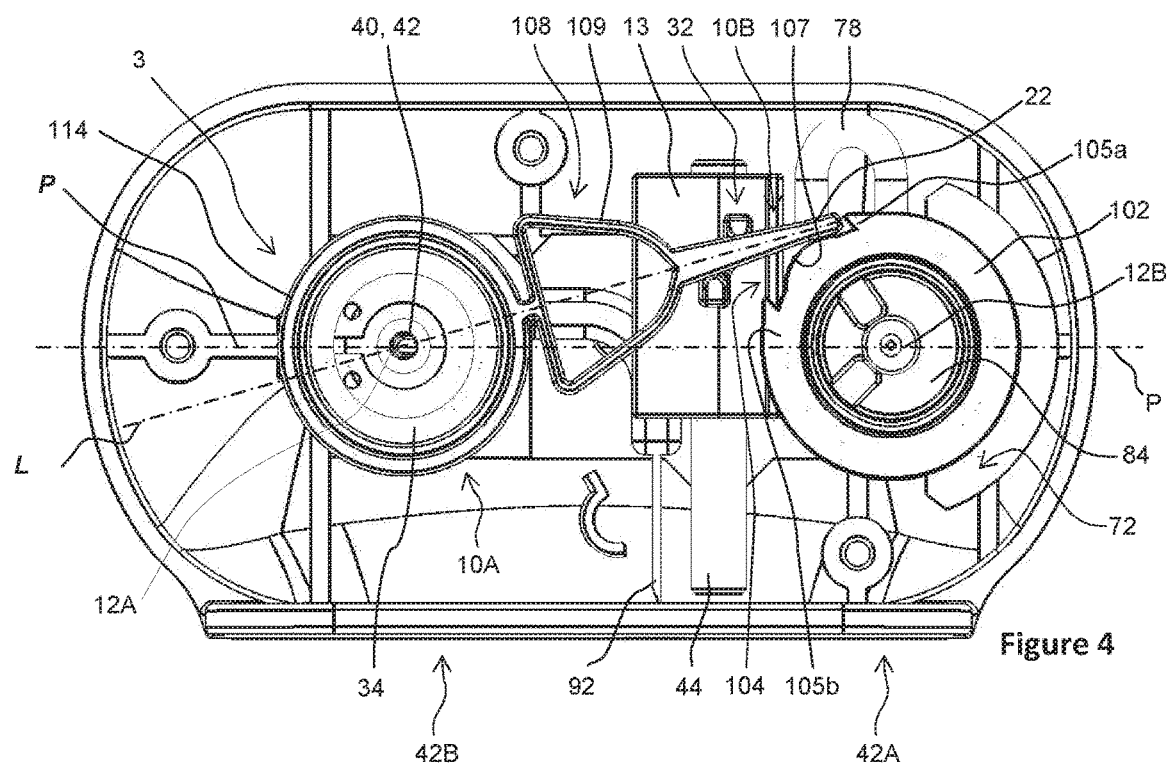
FIGS. 4-7 are side cross-sectional views of the subcutaneous delivery mechanism of FIG. 3 in various operational states.

Referring to FIGS. 3-7, and 16b, a first side 42B of the support member 14 supports the reservoir coupling system 3. The coupling system 3 comprises a coupling extension 34, having an internal bore 36 which is shaped to receive a head (not shown) of the reservoir and a seal member 38 to hermetically seal the reservoir within the bore 36 once received. As shown in FIG. 4, an inlet needle 40 is arranged within the bore 36 such that it is operable to penetrate a septum of the reservoir as the reservoir is inserted along an axis 42 of the bore. It will be appreciated that in other embodiments other suitable coupling configurations may be used, for example, the coupling may comprise a needle-less coupling, such as a Luer taper coupling. The needle 40 is arranged in fluid communication with an outlet (not shown). The outlet is in fluid communication with a supply conduit 50, which transfers fluid from the reservoir to a pump engine 72. In the example embodiment the supply conduit 50 may conveniently be formed integrally with the support member 14, as best seen in FIGS. 2 and 3. However, the supply conduit may alternatively be a separable component. An exterior surface portion of the reservoir coupling extension 34 may function as a bearing that forms part of a pivoted connection 12 between the support member 14 and an actuator 106 of a needle actuation mechanism 10, which will be discussed in more detail in the following.

Referring to FIGS. 2-4, the pump 7 comprises a pump engine 72 which is provided at a second side 42A of the support member 14. The pump engine 72 is operable to pump fluid from the reservoir to a needle 92 for subcutaneous delivery. In this example the pump engine 72 comprises a drive interface 84 configured to dock with an engine interface (not shown) of the pump drive (not shown) such that torque from the pump drive is transferred to the pump engine 72 to drive the pump engine. A suitable pump engine and drive unit is provided in WO 2005/039674, which is incorporated herein by reference. However, it will be appreciated that other rotary pump engines and pump drives may be used. Moreover, the pump engine could be permanently coupled or attached to a pump drive, and/or the drive could be incorporated in the delivery unit 2 and receive power, for instance via electrical contacts or by induction from a power source (not shown) mounted in the base unit.

As best seen in FIGS. 2 and 3, an inlet 74 of the pump engine 72 receives fluid from the supply conduit 50 and an outlet 76 of the pump supplies fluid to the needle 92 via a delivery conduit 78. A rotary member 102 of a needle actuation mechanism 10 is mounted to the pump engine 72 such that rotation during actuation of the pump engine causes rotation of a rotary member 102, as will be discussed in more detail in the following. It will be appreciated that in other embodiments the rotary member may not be mounted directly onto the pump engine, for example it may be coupled to the pump engine via a geared system, or may alternatively be driven separately from the pump.

Referring to FIGS. 2 and 3, the subcutaneous delivery mechanism 9 comprises a needle 92 adapted for transdermal delivery of the fluid from the reservoir. At a first end, the needle 92 comprises an inlet which is in fluid communication with the delivery conduit 78, and at an opposed second end the needle is configured to pierce through a patient's skin and deliver the fluid.

The subcutaneous delivery mechanism 9 further comprises a needle actuation mechanism 10 comprising the rotary member 102, 302 coupled to the pump engine 72 and the actuator 106, 306 which is pivotally mounted to the coupling extension 34 of the reservoir coupling system 3. In an exemplary embodiment as can be seen in FIG. 3, at a pivot portion 10A of the actuator 106, 306 the pivoted connection 12 comprises an annular ring 114 that extends around the coupling extension 34. It will be appreciated that the actuator may alternatively be pivotally connected to other parts of the support member. At an engagement portion 10B the actuator comprises an extension 22. The extension 22 is configured to engage with shoulders 105a, 305a, 105b, 305b of an engagement member 104, 304 of the rotary member as will be discussed in more detail following.

Figure 5:
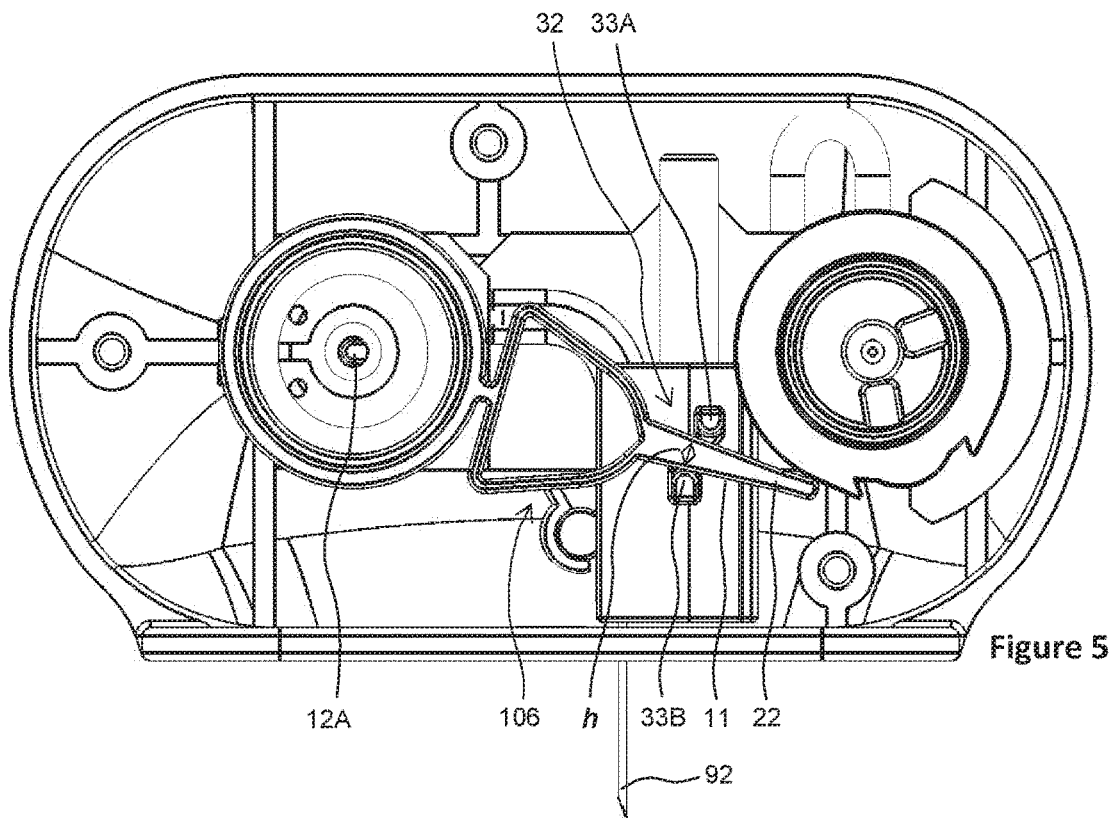

In the embodiment illustrated in FIGS. 2 to 12, the needle actuation mechanism 10 may further comprise a deformable member 108, which is operable to move between an undeformed extended position and a deformed retracted position on engagement of the engagement member 104 and the engagement portion 10B. Referring to FIGS. 4 and 5 in particular, in an embodiment the deformable member comprises a deformable portion 109 on the actuator 106. The deformable portion 109 is arranged between the pivot portion 10A and engagement portion 10B. The deformable portion 108 is configured to allow the actuator to expand and contract axially along an axis L that extends between the engagement portion 10B and pivot portion 10A. In an advantageous embodiment, the deformable portion 108 is configured to allow the actuator to expand and contract elastically. In the latter configuration, the deformable portion 108 may advantageously comprise an elastic bow portion 109 comprising elastically bendable arms surrounding an interior space that allows the elastic bow portion 109 to deform into the interior space. In FIGS. 3-9 the elastic bow portion 109 has an arrow tip shaped configuration, however a range of suitably shaped configurations are possible, as exemplified in FIGS. 10a to 10c, wherein various configurations of deformable portions are shown. FIG. 10a shows a deformable portion 108a with an elastic bow portion 109a which is a similar shape to that of the elastic bow portion 109 in the embodiments of FIGS. 3 to 9. However, in the embodiment of FIG. 10a a rear section 111a of the deformable portion 108a is curved as opposed to being straight such that it extends partially into the elastic bow portion 109a. FIGS. 10b and 10c show variants of deformable members 108b, 108c that comprise several diamond shaped portions.

FIG. 10d shows a deformable portion 108d that comprises a member in the form of an elongated slot with curved ends. A first end 109d of the member is biased into abutment with a coupling extension 42 by means of an elastic biasing member 111d, which in this embodiment is a leaf spring. Arm portions Ld that interconnect the first end 109d and second end 115d are configured to guide the deformable portion 108d as it presses against the elastic biasing member 111d.

FIG. 10e shows an alternative embodiment of a deformable portion 108e that comprises a first guide member 109e at a first end of the deformable portion which is adapted to slidably engage with a second guide member 111e at a second end of the deformable portion. In this example the first guide member and second guide member correspond to a piston adapted to slide within a housing. However, the first guide member and second guide member may comprise other slidable configurations such as an insert slidable within a channel. A biasing means Le may bias the first and second guide member into the extended position, such that they can contract against the biasing member to the retracted position. The biasing member may, for example, comprise a spring or pneumatic system. To prevent over extension of the first guide member a restraining means (not shown) may be provided. For example, the restraining means comprises a stop that engages in the extended position or alternatively, in the embodiment comprising the spring, the spring is mechanically connected to the first and second guide such that over extension of the spring prevents over extension of the first guide member.

In the embodiments, the deformable portion 108 is configured such that it can be deformed most easily in the axial direction extending through a pivot axis 12A of actuator, but has a greater rigidity in the direction orthogonal to the axial direction. In this way the position of the actuator is controlled during deformation. A suitable material for the actuator is a plastic such as LD-PE, POM or PA.

Referring to FIGS. 4-9 in particular, the rotary member 102 comprises a substantially circular periphery with the engagement member 104 disposed on part of its circumference. A first portion 105A of the engagement member comprises an angled catch which protrudes outwardly in a radial direction and protrudes tangentially in a first direction. Accordingly, the shape of the first portion 105A is such that when the rotary member 102 is rotated in the first direction (which in the figures is an anti-clockwise direction as shown in FIGS. 8a-c), the extension 22 of the actuator 106 is securely engaged and is subsequently moved with the rotary member 102.

The engagement member 104 further comprises a corresponding second portion 105B, which is configured in a similar fashion to that of the first portion 105A. However, the second portion protrudes tangentially in an opposed second direction. Accordingly, the shape of the second portion 105B is such that when the rotary member 102 is rotated in the second opposed direction (clockwise as shown in FIGS. 9a-c), the extension 22 of the actuator 106 is securely engaged and is subsequently moved with the rotary member 102.

As shown in FIGS. 4, 5, 8 and 9, the actuator 106 is movable such that the extension 22 of the actuator moves between a first extension position (FIG. 4, wherein the extension is on a first side of a line P extending between the pivot axis 12A of the actuator 106 and a rotational axis 12B of the rotary member 102) and a second extension position (FIG. 5, wherein the extension is on the opposite side of the line P).

Figure 6:
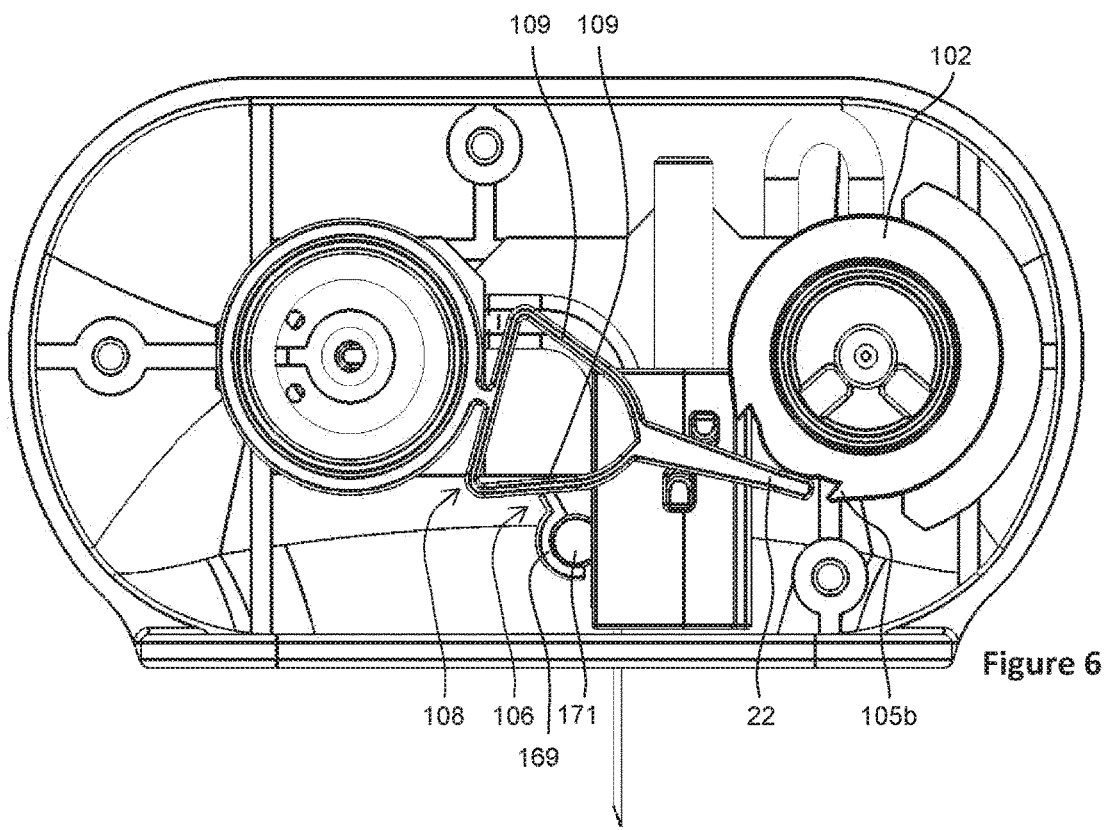
Figure 7:
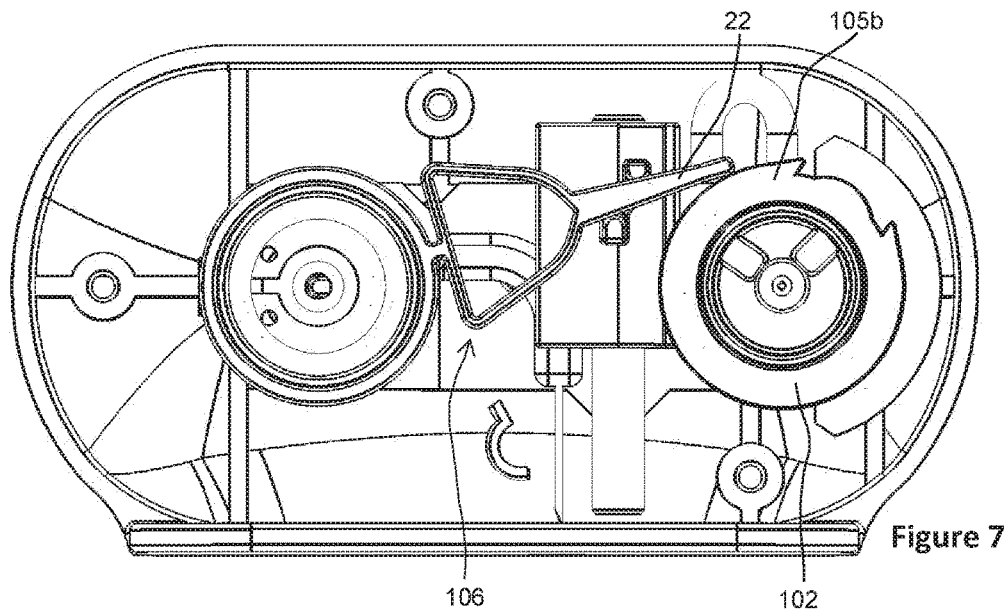

Referring to an exemplary embodiment as seen in FIG. 4, with the extension in the first extension position, the first portion 105A of the rotary member 102 is able to engage the extension when rotated in the first direction such that the extension is at least partially driven to the second extension position, as shown in FIG. 5. Referring to FIG. 6, the extension may then be returned to the first extension position by rotating the rotary member in the reverse second direction such that the second portion 105B of the rotary member 102 is able to engage the extension and at least partially drive the extension to the first extension position, as shown in FIG. 7.

The shape of the engagement member 104 is such that when the actuator 106 is arranged with the extension in the second extension position, rotation of the rotary member in the first direction does not substantially displace the actuator. Likewise, the shape is such that when the actuator is arranged with the extension in the first position, rotation of the rotary member in the second direction does not substantially displace the position of the actuator. To achieve such an effect the engagement member 104 comprises a lip 107 that is arranged between the first 105A and second 105B portion. The lip projects outwardly in the radial direction, and acts to minimize the difference between the radial distance of the extension from the axis of rotation of the rotary member 102 when in contact with a regular portion of the rotary member 102, and the radial distance when in contact with the engagement member.

Figure 8:
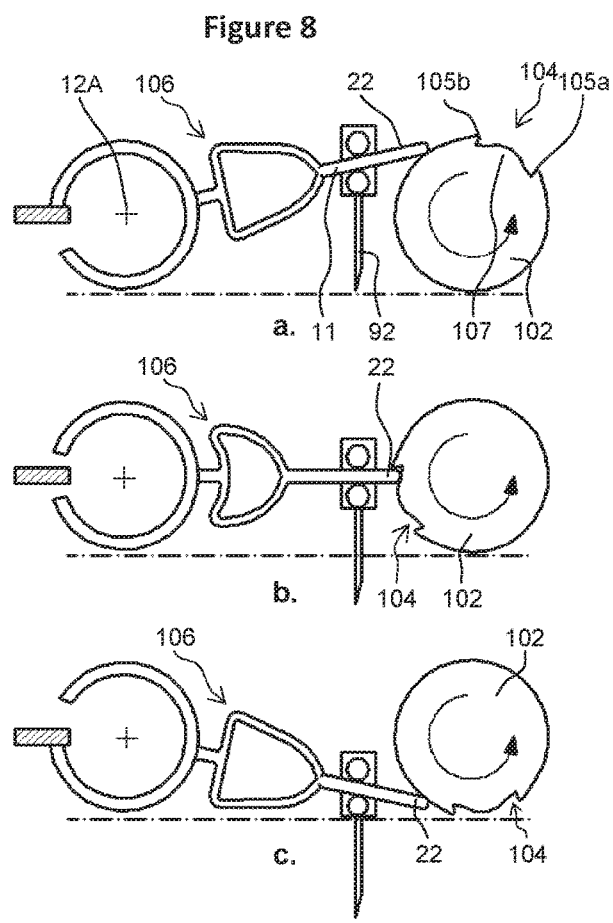
FIGS. 8 and 9 are diagrammatic views of the subcutaneous delivery mechanism of FIG. 3 in various operational states.
Figure 9:
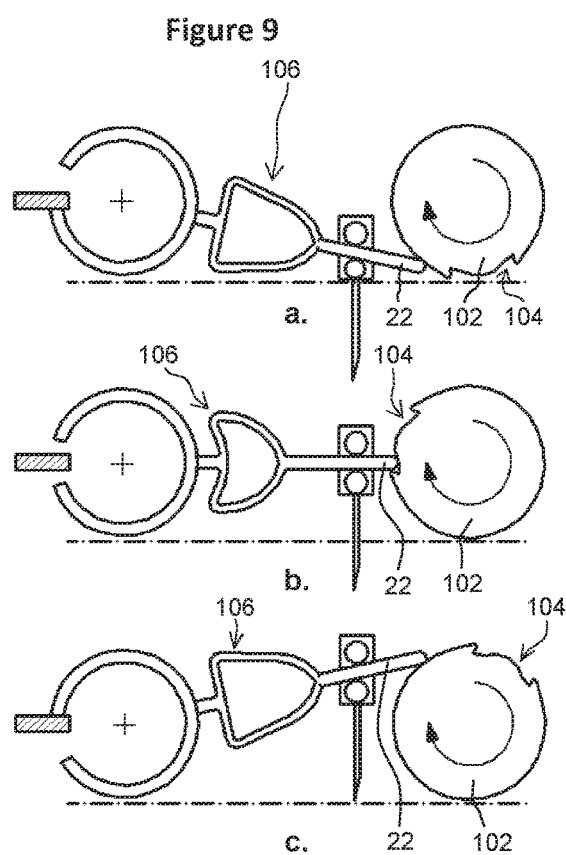

Referring to FIGS. 8 and 9 in particular, the actuator 106 further comprises an actuation portion 11 to actuate the needle 92. The actuation portion 11 is moved between a first and second position corresponding to the extension being in the first and second extension positions. In the exemplary embodiment the actuation portion 11 is arranged between the pivot portion 12 and the extension 22 of the actuator. However, it may be alternatively arranged, for example, the actuation portion may be positioned on an extension that protrudes from the pivot portion 10A.

The deformable portion 108 enables the actuator 106, and more particularly the actuation portion 11 of the actuator, to snap between first and second positions in a bi-stable manner. In more detail, with the extension 22 in the first or second extension position (FIGS. 8a, 9a, 8c, 9c), the deformable portion is in the extended position, where it does not apply any substantial axial force, along axis 22 to the extension 22, the applied force being merely sufficient force to retain the extension in the correct position. However, as the extension 22 is driven intermediate the first and second extension positions (FIGS. 8b, 9b) the axial force increases to a maximum as the deformable portion is driven to the retracted position. As the extension is subsequently driven to the first or second extension portion the force is relieved. Accordingly, the first and second extension positions correspond to the bi-stable positions.

In an embodiment (not shown) the needle 92 may be directly connected to the actuation portion 11, such that it is moved between the extended and retracted position as the actuation portion 11 is moved between the first and second position. Alternatively, as shown in the embodiment of FIGS. 1-9, the actuation portion 11 is configured to move the needle support 13 to which the needle 92 is mounted. Referring to FIGS. 3 and 4 in particular, the actuation portion 11 engages with an engagement member 32 of the needle support 13. The needle support 13 is slidably movable relative to the support member 14 such that movement of the actuation portion 11 between the first and second position moves the needle 92 in a linear fashion between the corresponding extended and retracted positions. Slidable movement of the needle support 13 is achieved by a guide 44 of the support member 14, which is inserted into and is operable to move along a channel 124 of the needle support 13. The needle support 13 is rotationally constrained about an axis along which it slides by means of a keyway 45 which extends along the guide 44 and engages with the ends of the channel 124. It will be appreciated that slidable movement may be achieved by other means, for example, the guide may be arranged on the support member and the channel may be arranged on the needle support.

As best seen in FIG. 5, the actuator engagement member 32 of the needle support 13 is configured such that when the needle 92 is in the extended position, the needle support 13 is isolated from movement of the actuator caused by rotation of the rotary member in the first direction. The engagement member 32 comprises a first extension 33A and a second extension 33B that are arranged on opposed sides of the actuation portion 11. The first and second extensions are staggered such that when the actuation portion 11 is in the second position, a gap h between the first and second extension is partially occupied by the actuation portion. With such an arrangement the actuation portion can displace small amounts within the gap h without displacing the support member 13.

Referring to FIGS. 1 and 2 in particular, the delivery unit 2 further comprises a support member housing 15 which extends around the support member 14 and associated components leaving the pump engine 72 drive unit engagement portion 84 exposed such that it may receive the pump engine interface of the pump drive. Moreover, the bore 36 of the coupling extension 34 remains exposed such that it may receive the reservoir. The delivery unit 2 further comprises a guide plate 52 for locating a housing 19 of the base unit 16 when connecting the base unit 16 and delivery unit 2 together. An underside of the guide plate 52 may comprise an adhesive (not shown) for adhering the delivery unit 2 to a patient. The base unit 16 comprises a control unit 20 for controlling the pump drive to supply the required dosage regimen.

Referring to FIGS. 11 and 12, an alternative embodiment of the needle support 30 is provided, wherein the needle support comprises a plate 220 having an actuator engagement member 232 that comprises first 233A and second 233B extensions that engage the actuation portion 22 of the actuator 106 in the manner discussed above. The plate 220 comprises first and second channels 224A, 224B which are arranged to engage corresponding opposed guides 244A, 244B. The guides 244A, 244B are arranged such that the guide 244A extends from the coupling system 3 and the guide 244B extends from the pump engine 72.

The delivery conduit 78 comprises a flexible member operable to maintain fluid communication between the pump outlet 76 and needle 92 as the needle support 13 moves the needle between the extended and retracted positions. Referring to FIG. 13, an embodiment of the transfer conduit is shown, wherein the transfer conduit 378 is formed integrally with the needle 92, and is in fluid communication with the pump outlet 376. Since the material of the needle is inherently inflexible (so that it may be extended trans-dermally without buckling) a sufficiently flexible transfer conduit 378 is achieved by manipulating the geometry of the conduit. For instance, in the embodiment the transfer conduit comprises a 'U' shaped portion 380. Referring to FIG. 14, another embodiment of the transfer conduit is shown, wherein the transfer conduit 478 is formed separately from the needle 92. In this embodiment the transfer conduit 478 is made from a flexible material, such as a plastic, and consequently it may extend more or less directly between the needle 92 and pump outlet 476.

In some of the aforementioned exemplary embodiments, the engagement member of the rotary member comprises a first portion 105A and a second portion 105B which engage with the extension 22 of the actuator 106 depending on the position of the extension and direction of rotation of the rotary member. In this way the needle actuation mechanism is operable to both retract and extend the needle. However, it will be appreciated that it is within the scope of the invention that other configurations are possible. For example, if the needle actuation mechanism is required only to move the needle from the retracted position to the extended position then the second portion 105B may be omitted. Alternatively, if the needle actuation mechanism is required only to move the needle from the extended position to the retracted position then the first portion 105A may be omitted. Furthermore, more than one first portion 105A and/or second portion 105B may be provided on the rotary member. An advantage of such a system is that, in comparison with a single first portion 105A and/or single second portion 105B, the needle can be actuated between the extended and retracted positions by in general rotating the rotary member to a lesser degree.

Figure 15:
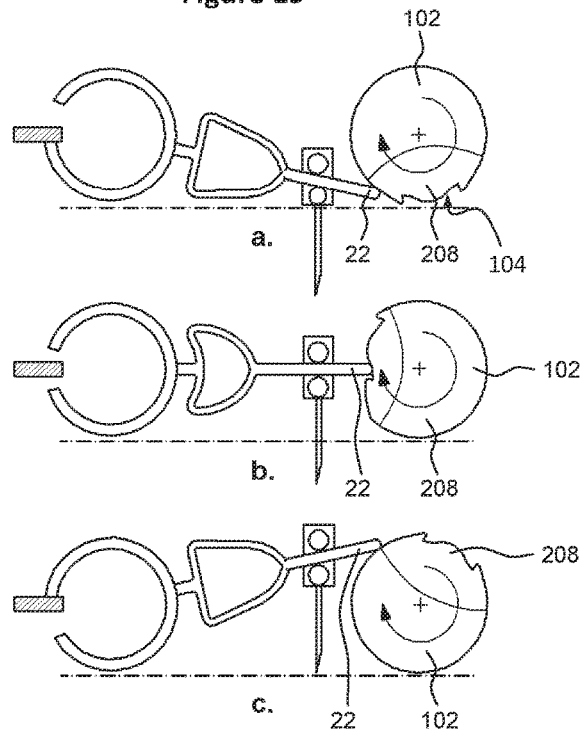
FIG. 15 is a diagrammatic view of an alternative subcutaneous delivery mechanism according to an embodiment of the invention.

In some of the aforementioned exemplary embodiments, the actuator of the needle actuation mechanism is described as having a deformable portion. However, it will be appreciated that it is within the scope of the invention that other configurations are possible. For example, in one embodiment the rotary member comprises a deformable portion. With such an arrangement, the engagement member of the rotary member may be formed at least partially from a flexible material, or may be flexibly connected to the rotary member. In this way, during rotation of the rotary member, and as the actuation portion is moved between the first and second positions, part of the rotary member can deform whilst the actuator remains substantially un-deformed. An example of such a system is shown in FIGS. 15a-c, wherein the rotary member 102 comprises a deformable portion 208, for instance the rotary member may comprise a compressible material. As shown in FIG. 15b the deformable portion is deformed when the extension 22 is moved between the first (extended) position (FIG. 9c) and second (retracted) position (FIG. 9a).

In a further example, neither the actuator nor the rotary member comprises a deformable portion. With such an arrangement, the rotary member may act a cam such that its engagement member engages the engagement portion of the actuator to move the actuation portion of the actuator between the first and second positions. It will be appreciated that the actuator may be biased into contact with the rotary member by means of a biasing member such as a spring. In this way as a distance of a periphery of the engagement member from the center of rotation of the rotary member increases, the actuation portion can be moved from one of the first or second positions, and as the distance decreases it can be moved from the other of the first or second positions. However, a biasing member is not essential. For example, the actuation mechanism may only be operable to move the actuation portion from the first to the second position to move the needle from the retracted position to the extended position. Alternatively, the actuation mechanism may only be operable to move the actuation portion from the second to the first position to move the needle from the extended position to the retracted position.

It will also be appreciated that the deformable portion is not limited to being elastically deformable. For example, it may alternatively be at least in part plastically deformable. Such a configuration is advantageous in ensuring the needle actuation mechanism can only perform a single extension and/or retraction. For instance, part of the deformable portion when on the actuator and/or on the engagement member of the rotary member may be permanently deformable such that after a single movement of the actuation portion from one of the first or second positions to the other of the first or second positions it is no longer operable to correctly engage with the engagement portion of the actuator.

Referring to FIGS. 16a to 17f, another embodiment of a needle actuation mechanism 100 is illustrated. In this embodiment, the actuator 306 and rotary member 302 are configured to provide protection against reuse of the subcutaneous delivery mechanism 9. Protection against reuse is provided by an arrangement configured to prevent the actuator 306 from leaving the retracted position after the needle 92 has been extended and then retracted after a first use. After first use, the actuator 306 can no longer be engaged by the engagement member 304 of the rotary member 302 to move the actuator to the extended position, thus avoiding potential injury or contamination. Additionally, this provides safety for a user by ensuring that the needle 92 to be inserted has not been previously used and is thus sterile.

The needle actuation mechanism 100 with protection against reuse is based on a special geometry of the rotary member 302 that brings the actuator 306 upon the retraction of the needle 92 into a terminus position. A guide protrusion 380 decouples the actuator 306 from engagement with the shoulder 305a of the engagement member 304 such that a needle support 13, to which the needle 92 is mounted, and the needle 92 are immovably contained within the housing of the drug delivery device 1 and cannot be brought into an extended position again. The rotary member 302 comprises a first track 390 and axially offset therefrom a second track 391 around the outer circumference of the rotary member 302. The engagement portion 10B of the actuator 306 runs along the first track 390 during first use, including the steps of needle insertion, drug delivery, and beginning of the retraction rotation. The engagement shoulder 305a of the engagement member 104 is provided on the first track only, such that when the engagement portion 10B of the actuator is shifted axially across to the second track 391, there is no shoulder to catch the tip of the engagement member 10B and it can slide smoothly around the second track 391. Hence, the engagement member 10B travels along a first track 390 during insertion and along a second track 391 after first use.

The rotary member 302 is provided with an engagement member 304 in the form of a slot with an axial width W spanning across the first track 390 and the second track 391. The engagement member 304 comprises a transfer cam surface 305c configured to displace the engagement portion 10B of the actuator 306 in the axial direction A of the rotary member 302 (i.e. parallel to the axis of rotation of the rotary member) such that the engagement portion 10B can be moved from the first track to the second track. The transfer cam portion 305c of the engagement member 304 presents a sloped surface that forces the engagement portion 10B of the actuator in the axial direction. The slot forms the shoulder 305a of engaging member 304 in the first track of the rotary member 302, and in the second track the transfer cam surface 305c to transfer the engagement portion 10B of the actuator 306 from the first track to the second track, as well as the retraction shoulder 305b to engage the engagement portion 10B during reverse rotation for retraction of the needle.

The first track 390 and the second track 391 may be arranged in a distinctive manner around a first portion D of the outer circumference of the rotary member 302, and joined along the remaining portion J of the circumference.

A locking protrusion 380 is fixedly mounted to the support member 14 and comprises a locking shoulder 381 arranged to engage the actuator in the retracted position after first use and block the lateral movement of the actuator engagement portion back to the first track. The protrusion 380 advantageously prevents the actuator 306 from changing tracks after the needle 92 has been retracted, whereby the protrusion 380 blocks movement of the actuator in the axial direction A of the rotary member 302.

Figure 16C:
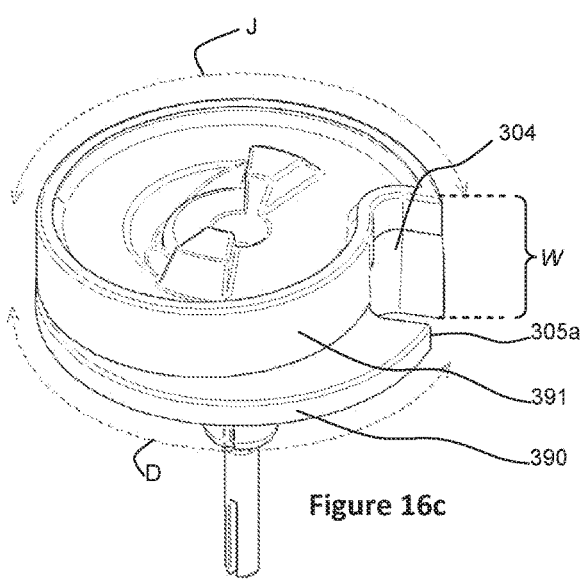
FIG. 16c is a perspective view of a rotary member according to an embodiment of the invention, having a first track and a second track.
Figure 16A:
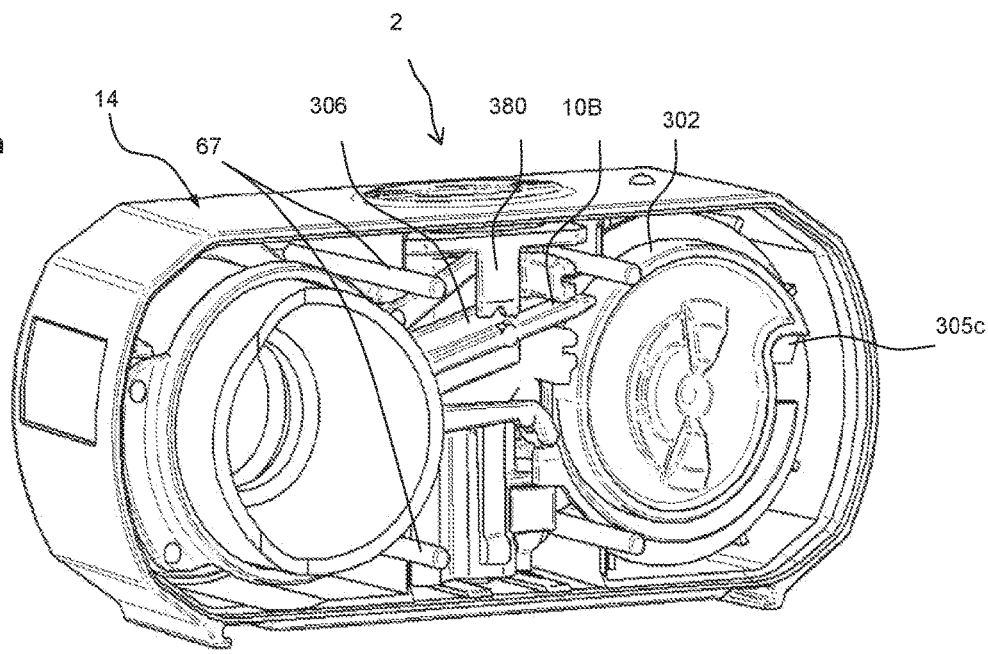
FIG. 16a is a perspective view of a delivery unit of a drug delivery device according to another embodiment of the invention.

Additionally, as best seen in FIGS. 16b and 17a, 17b and 17d, the actuator 306 may be further configured to be in constant mechanical contact with the rotary member 302 and with a certain force. This contact is preferably to be maintained during the operational life of the delivery unit 2. For this purpose, the actuator 306 may for instance be provided with a first spring arm 395 and a second spring arm 396 located on each side of the engagement portion 10B of the actuator 306. The springs 395, 396 can be made of a polymeric material, such as plastics, which is selected based on an e-module with a low density relaxation, or comprise metal. The spring arms are configured to press against a fixed member (e.g. posts 67 as shown in FIG. 16a, or top or bottom wall) on the support body 14 when in the fully retracted or park position and when in the extended or drug delivery position.

Additionally, as illustrated in FIG. 19, the geometry of the rotary member 302 may be further configured such that the contact force between the actuator 306 and the rotary member 302 is different in different angular positions the rotary member 302. As illustrated in FIG. 19, the rotary member can be provided with an indent 398 in order to relax the actuator 306 in a specific position in relation to the rotary member 302. In a preferred embodiment, the indent 398 is aligned with the actuator 306 when the actuator 306 is in the initial park position before use. The actuator 306 and the first leaf spring 395 and the second leaf spring 396 (see FIGS. 18a-18c) can therefore be relaxed before the delivery unit 2 is brought into use, such that the storage life of the unused delivery unit 2 can be extended by an increased durability of the actuator 306.

The needle support member 13 may have a small play in its guidance. When the needle is inserted and the pump is delivering fluid, the rotary member 102, 302 is rotating in the pumping direction of rotation and the actuator 106, 306 may oscillate due to the contact with the engagement member 104, 304 on the periphery of the rotary member 102, 302. In order to avoid or reduce the oscillation transferred from the actuator 106, 306 to the needle support member 13 and the needle 92, the actuator may be held in the extended position by a releasable connection, for instance an elastic snap lock connection formed by a protrusion 171, 371 engaging in a recess 169, at least one of the protrusion or recess being elastically deformable or elastically supported. For instance in the embodiment illustrated in FIG. 16b the protrusion 371 is mounted on an elastic arm 373 fixed to and forming part of the needle support member 13 and the recess (not visible in the illustrated views) is formed on the support 14. The snap lock connection removes the play in the guidance between the actuator 306 and the needle support member 13 such that oscillation of the actuator 306 is reduced.

In the exemplary embodiments illustrated in FIGS. 18b and 18c, the second spring arm 396 may be provided with a bent end 397 adapted to press against a surface of the support 14. In the variant of FIG. 18c, a metallic leaf spring forms the spring arms to provide greater spring force or a better stress/strain relationship than integrally formed polymer spring arms.

Now referring to FIGS. 17a to 17f in conjunction with FIG. 16b, steps of an insertion and retraction process performed by an exemplary embodiment of a needle actuation mechanism 100 are illustrated. In the illustrated example, the first track 390 of the rotary member is used for insertion and the second track 391 of the rotary member is used for retraction.

Figure 17A:
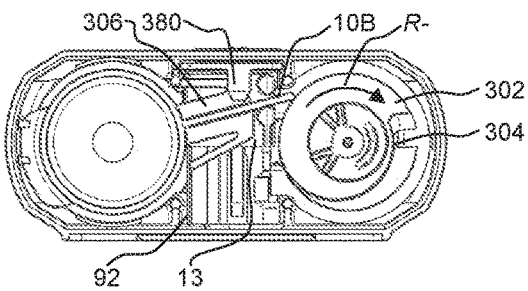
FIGS. 17a to 17f are cross sectional views of a needle actuation mechanism according to an embodiment the present invention during storage or fluid refill (FIG. 17a), needle insertion (FIG. 17b, 17c), drug delivery (FIG. 17d), needle retraction (FIG. 17e), and end position (FIG. 17f).
Figure 17B:
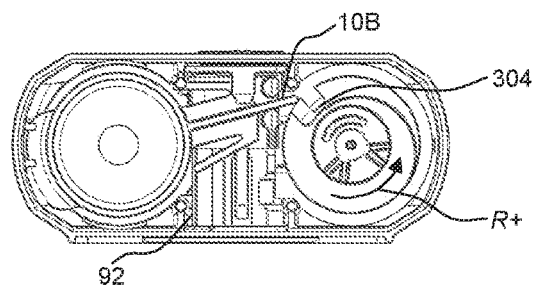
Figure 17C:
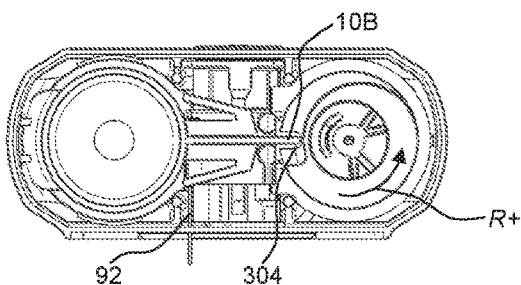
Figure 17D:
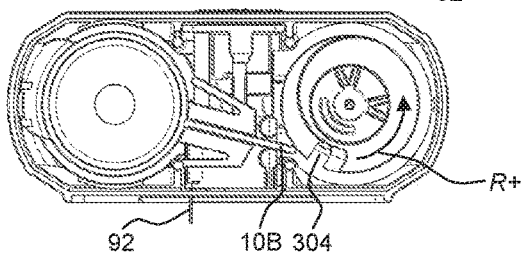

In a park position as illustrated in FIG. 17a, the actuator 306 is initially positioned on the first track 390 whereby this allows a possible drug transfer from a supply tank to the reservoir 303 using the pump engine rotating in the reverse direction R−. The engagement portion 10B of the actuator 306 is located on the first track 390 of the rotary member, 302 while the rotary member 302 is turning in a reverse direction R− allowing refilling direction.

In the illustrated example, the needle insertion process is initiated as the pump shaft starts turning the rotary member 302 in a positive (pumping) direction R+ and is completed as the engagement shoulder 305a engaging with the engagement member 10A of the actuator 306 until the needle support member 13 moves from the retracted to the extended position such that the needle 92 extends out of the housing and penetrates the skin of a user. During the drug delivery, the rotary member 302 can continue rotating in the positive direction R+ without being caught.

Figure 17E:
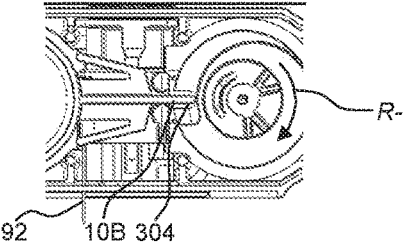
Figure 17F:
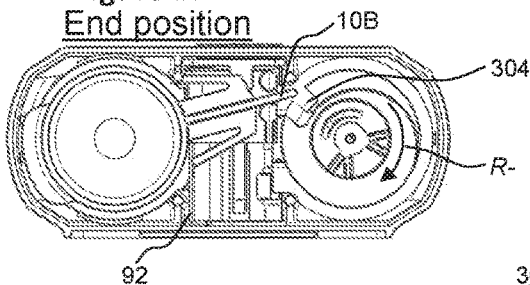
Figure 17F:
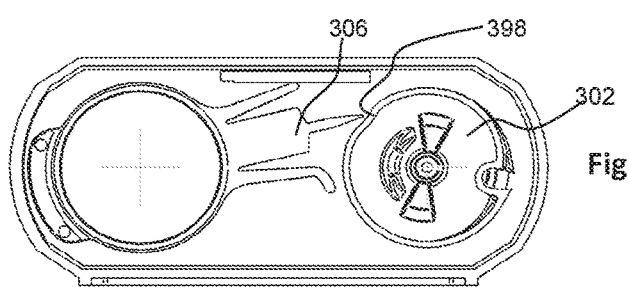

As illustrated in FIGS. 17e to 17f, in conjunction with FIG. 16b, the needle retraction process is initiated when the rotary member 302 changes direction such that it rotates in a reverse direction R−. The retraction shoulder 305b of the engagement member 304 catches the tip of the actuator which then is biased in the axial direction A by the cam portion 305c into the second track 391. As shown in FIG. 17f, in conjunction with FIG. 16b, as the engagement portion 10B of the actuator 106 moves upwards, it is caught on an opposite side of the protrusion 380 than when in the initial position shown in FIG. 17a. The protrusion 380 then prevents the engagement portion 10B of the actuator 306 to displace axially back over the first track and thus the tip of the actuator 306 can no longer be caught by the engagement shoulder 305a.

If the drug delivery device 1 is operated in order to achieve a subsequent insertion with the same needle, there is no engagement shoulder on the second track in the pumping direction R+ for the actuator 306 to get caught into. Hence, the rotary member cannot activate the actuator 306 to perform an insertion. Notably, as best seen in FIG. 16c, the second track of the pump shaft is provided with a geometry that gradually modifies the radius as it progresses away from the retraction shoulder 305b.

We claim:

1. A delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position, the actuation mechanism comprising a rotary member having an engagement member rotatable relative to a support member, and an actuator comprising a pivot portion, an actuation portion extending from the pivot portion, and an engagement portion extending from the actuation portion, the actuation portion and engagement portion pivotally connected to the support member via the pivot portion, wherein the actuation mechanism is actuated by rotation of the rotary member and wherein the engagement member and engagement portion are configured to engage upon rotation of the rotary member to pivot the actuation portion between first and second positions and to thereby move the subcutaneous delivery member between the corresponding retracted and extended positions.

2. The delivery unit according to claim 1, wherein the engagement member of the rotary member and engagement portion of the actuator are configured such that rotation of the rotary member in a first direction (R+) causes the actuation portion of the actuator to move the subcutaneous delivery member from the retracted position to the extended position, and such that rotation of the rotary member in a second direction (R−) causes the actuation portion of the actuator to move the subcutaneous delivery member from the extended position to the retracted position.

3. The delivery unit according to claim 1, wherein the actuation mechanism further comprises a subcutaneous delivery member support unit supporting the subcutaneous delivery member comprising an actuator engagement member and a first guide member, the actuator engagement member configured to be engaged with the actuation portion of the actuator, the first guide member slidably engaged with a second guide member of the support member.

4. The delivery unit according to claim 1, wherein the delivery unit further comprises a pump engine configured to pump a fluid to the subcutaneous delivery member by means of a rotary action, the pump engine being coupled to the rotary member.

5. The delivery unit according to claim 1, wherein the engagement portion of the actuator comprises an extension, the engagement member comprising a first engaging portion configured to engage the extension when the rotary member is rotated in a first direction (R+) and the extension is arranged on a first side of a line (P) between a rotational axis of the rotary member and a pivot axis of the pivot portion in the first position corresponding to the retracted position, and being further configured such that upon further rotation in the first direction the extension is moved from the first position to the second position corresponding to the extended position, wherein in the second position the extension is arranged on an opposed second side of said line (P).

6. The delivery unit according to claim 5, wherein the engagement member and extension of the actuator are configured such that when the extension is in the second position, rotation in the first direction does not substantially move the actuation portion of the actuator.

7. The delivery unit according to claim 5, wherein the engagement member of the rotary member further comprises a second engaging portion configured to engage the extension when the rotary member is rotated in a second direction (R−) and the extension is arranged on the second side of said line (P), and being further configured such that upon further rotation in the second direction the extension is moved from the second position to the first position.

8. The delivery unit according to claim 5, wherein the first and second engaging portions are in the form of angled catches or shoulders formed in the circumference of the rotary member.

9. The delivery unit according to claim 1, wherein the actuation mechanism comprises an elastically deformable member allowing relative elastic movement between the engagement portion of the actuator and the engagement member of the rotary member.

10. The delivery unit according to claim 1, wherein the delivery unit further comprises a coupling system having a coupling extension that comprises a bearing surface pivotally supporting a ring of the pivot portion, and an interior reservoir head mounting portion for coupling a reservoir to the delivery unit.

11. The delivery unit according to claim 1, wherein a needle support member and support comprise a releasable connection formed by a protrusion engaging in a recess, at least one of the protrusion or recess being elastically deformable or elastically supported, configured for releasably holding the needle support member in the second position.

12. The delivery unit according to claim 1, wherein the actuator comprises spring arms configured to elastically bias against a portion of the support member in the first and second positions.

13. A delivery unit of a drug delivery device, the delivery unit comprising a subcutaneous delivery mechanism having a subcutaneous delivery member and a subcutaneous delivery member actuation mechanism being operable to move the subcutaneous delivery member between a retracted position and an extended position, wherein in the extended position the subcutaneous delivery member is arranged to deliver a dosage of a fluid trans-dermally to a patient and in the retracted position the subcutaneous delivery member is arranged such that it is retracted from the patient, the actuation mechanism comprising:
  a rotary member rotatable relative a support member, the rotary member having an engagement member;
  an actuator connected to the support member, the actuator having an engagement portion; and
  a pump engine configured to deliver a fluid to the subcutaneous delivery member, the pump being rotatably drivable,
  wherein the engagement member and engagement portion are configured to engage upon rotation of the rotary member and the actuator is configured such that the engagement causes a subcutaneous delivery member actuation portion of the actuator to move between first and second positions, and to thereby move the subcutaneous delivery member between the corresponding retracted and extended positions, and wherein of the pump engine is connected to the rotary member.

14. A drug delivery device comprising a re-usable base unit including a pump drive, and a delivery unit according to claim 1, the delivery unit forming a non-reusable or single use disposable part separable from the base unit.

* * * * *